US00PP11475P

United States Patent [19]

Kientzler

[11] Patent Number: Plant 11,475

[45] Date of Patent: Aug. 8, 2000

[54] NEW GUINEA IMPATIENS PLANT NAMED 'KIPED'

[75] Inventor: Ludwig Kientzler, Gensingen, Germany

[73] Assignee: Paul Ecke Ranch, Inc., Encinitas, Calif.

[21] Appl. No.: 09/127,639

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 6,684 3/1989 Kientzler ..... Plt./318
P.P. 8,358 8/1993 Bull ..... Plt./318

*Primary Examiner*—Howard J. Locker
*Assistant Examiner*—Wendy A Baker
*Attorney, Agent, or Firm*—C. A. Whealy

[57] ABSTRACT

A new and distinct cultivar of New Guinea Impatiens plant named 'Kiped', characterized by its numerous salmon pink-colored flowers; upright and somewhat spreading growth habit; very freely branching, dense and bushy plant habit; and dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar named Kiped.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the proprietary selection identified as MF 42 as the male, or pollen parent, with the proprietary selection identified as MF 291 as the female, or seed parent.

The cultivar Kiped was discovered and selected by the Inventor as a flowering plant within the progeny of the stated cross in a controlled environment in Gensingen, Germany, in April, 1995.

Asexual reproduction of the new cultivar by terminal cuttings taken at Gensingen, Germany, has shown that the unique features of this new New Guinea Impatiens are stable and reproduced true to type in successive generations of asexual reproduction.

SUMMARY OF THE INVENTION

The following traits have been repeatedly observed and are determined to be the unique characteristics of 'Kiped'. These characteristics in combination distinguish 'Kiped' as a new and distinct cultivar:

1. Numerous salmon pink-colored flowers that are held above the foliage.

2. Upright and somewhat spreading growth habit; "V"-shaped.

3. Very freely branching, dense and bushy plant habit.

4. Dark green leaves.

Plants of the new New Guinea Impatiens are smaller, but have larger flowers than plants of the male parent, the proprietary selection identified as MF 42.

Compared to plants of the female parent, the proprietary selection identified as MF 291, plants of the new New Guinea Impatiens have darker-colored flowers and greener leaf color.

Plants of the new New Guinea Impatiens are similar in flower color to plants of the cultivar Bonaire, disclosed in U.S. Plant Pat. No. 9,137. However, in side-by-side comparisons conducted in Encinitas, Calif., plants of the new New Guinea Impatiens differed from plants of the cultivar Bonaire in the following characteristics:

1. Plants of the new New Guinea Impatiens are slightly taller, have longer lateral branches and internodes, and are not as outwardly spreading as plants of the cultivar Bonaire.

2. Plants of the new New Guinea Impatiens have shorter but broader leaves than plants of the cultivar Bonaire.

3. Leaves of plants of the new New Guinea Impatiens are slightly lighter green than leaves of plants of the cultivar Bonaire. Lower leaf surfaces of plants of the cultivar Kiped are green in color whereas lower leaf surfaces of plants of the cultivar Bonaire are red purple in color.

4. Flowers of plants of the new New Guinea Impatiens are slightly smaller and more rounded than flowers of plants of the cultivar Bonaire.

A detailed comparison of plants of cultivars Kiped and Bonaire appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new New Guinea Impatiens.

The photograph at the top of the sheet comprises a top perspective view of a typical plant of the cultivar Kiped.

The photograph at the bottom of the sheet comprises a comparison close-up view of typical flowers and leaves of the cultivars Kiped (left) and Bonaire (right). Flower and foliage colors in the photographs may differ from the actual colors due to light reflectance.

DETAILED BOTANICAL DESCRIPTION

Plants of the cultivar Kiped have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene-covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar Kiped.

*Commercial.*—New Guinea Impatiens cultivar Kiped.

Parentage:

*Male parent.*—Proprietary selection of *Impatiens hawkeri* identified as MF 42.

*Female parent.*—Proprietary selection of *Impatiens hawkeri* identified as MF 291.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Upright and somewhat spreading; "V"-shaped.

*Growth habit.*—Vigorous. Very freely branching, dense and bushy growth. Appropriate for 10 to 25-cm containers.

*Crop time.*—From planting of a rooted cutting, about eight weeks are required to produce a finished flowering plant in a 12.5-cm container.

*Plant size.*—Height: About 25 cm. Width or spread: About 31 cm.

*Lateral branches.*—Quantity: About 10. Length: About 20 cm. Diameter: About 8.5 mm. Internode length: About 5 cm. Color: 59B.

*Foliage description.*—Leaves simple, generally symmetrical, abundant, opposite or in whorls, horizontal to plant. Mostly flat. Length: About 10 cm. Width: About 4.4 cm. Shape: Elliptic with acuminate apex, attenuate base and serrulate margin with ciliation. Texture: Smooth, somewhat glossy. Color: Young foliage, upper surface: 146A. Young foliage, lower surface: 147C. Fully expanded foliage, upper surface: 147A to darker than 147A. Fully expanded foliage, lower surface: 147C. Venation, upper surface: 61B at leaf base; towards apex close to leaf color. Venation, lower surface: 61A. Petiole: Length: About 3.5 cm. Diameter: About 3 mm. Color: 60A to 60C.

Flower description:

*Flower type and habit.*—Salmon pink-colored flowers. Freely and continuously flowering. Flowers arise from leaf axils. Usually about 15 flowers and flower buds per lateral branch. Flowers positioned above the foliage and face mostly upward. Flowers slightly cupped and nearly rounded. Flowers persistent.

*Flowering season.*—Year-round under greenhouse conditions. In the garden, flowering is continuous from spring until fall. Flowers typically last less than one week depending on environmental and cultural conditions.

*Flower size.*—Length, vertical axis: About 5.2 cm. Width, horizontal axis: About 5.2 cm. Depth: About 1.75 cm.

*Flower buds.*—Length: About 1.8 cm. Diameter: About 9 mm. Shape: Ovoid. Color: 52A.

*Petals.*—Quantity: Five. Length: Upper petal: About 2.5 cm. Middle petals: About 2.7 cm. Lower petals: About 2.8 cm. Width: Upper petal: About 2.8 cm. Middle petals: About 3 cm. Lower petals: About 3.2 cm. Shape: Cordate with acute base and entire margin. Texture: Velvety, smooth. Color: When opening, upper surface: 54A to 54B; 57A to 57B at base. When opening, lower surface: 52D. Fully opened, upper surface: Towards margins, 54A to 54B; center darker, 52A to 52B; 57A to 57B at base; color fading to 54C to 54D. Fully opened, lower surface: 54B to 54C.

*Spur.*—Length: About 4.5 cm. Shape: Narrow and curved. Color: 59A/59B.

*Peduncles.*—Length: About 5.5 cm. Angle: Very acute. Strength: Strong. Color: 59A.

*Reproductive organs.*—Androecium: Stamen number: Five, anthers fused, filaments free. Anther shape: Obovate. Anther size: 3 mm by 5 mm. Anther color: 54D. Amount of pollen: Moderate. Pollen color: 2D. Gynoecium: Five-loculate fused. Pistil length: About 5 mm. Stigma color: 2D. Ovary color: 145A changing to 59A when anthers abscise.

Disease resistance: Under commercial conditions, resistance to pathogens has not been observed.

Seed development: Seed production has not been observed.

CHART A

| CHARACTERISTIC | 'KIPED' | 'BONAIRE' |
|---|---|---|
| GROWTH HABIT, PLANT SHAPE | Upright and somewhat spreading | Spreading |
| PLANT HEIGHT | About 25 cm | About 22 cm |
| PLANT WIDTH | About 31 cm | About 34 cm |
| LATERAL BRANCH LENGTH | About 20 cm | About 17 cm |
| INTERNODE LENGTH | About 5 cm | About 3.5 cm |
| LEAF LENGTH | About 10 cm | About 10.75 cm |
| LEAF WIDTH | About 4.4 cm | About 3.4 cm |
| LEAF COLOR, MATURE, UPPER SURFACE | 147A to darker than 147A | Darker than 147A |
| LEAF COLOR, MATURE, LOWER SURFACE | 147C | 59B |
| PETIOLE LENGTH | About 3.5 cm | About 2.75 cm |
| FLOWER SHAPE | Nearly round | Rounded rectangle |
| FLOWER DIAMETER | About 5.2 by 5.2 cm | About 5 by 6 cm |
| PEDUNCLE ANGLE | Very acute | Acute |
| PEDUNCLE COLOR | 59A | 60B |

It is claimed:

1. A new and distinct cultivar of New Guinea Impatiens plant named 'Kiped', as illustrated and described.

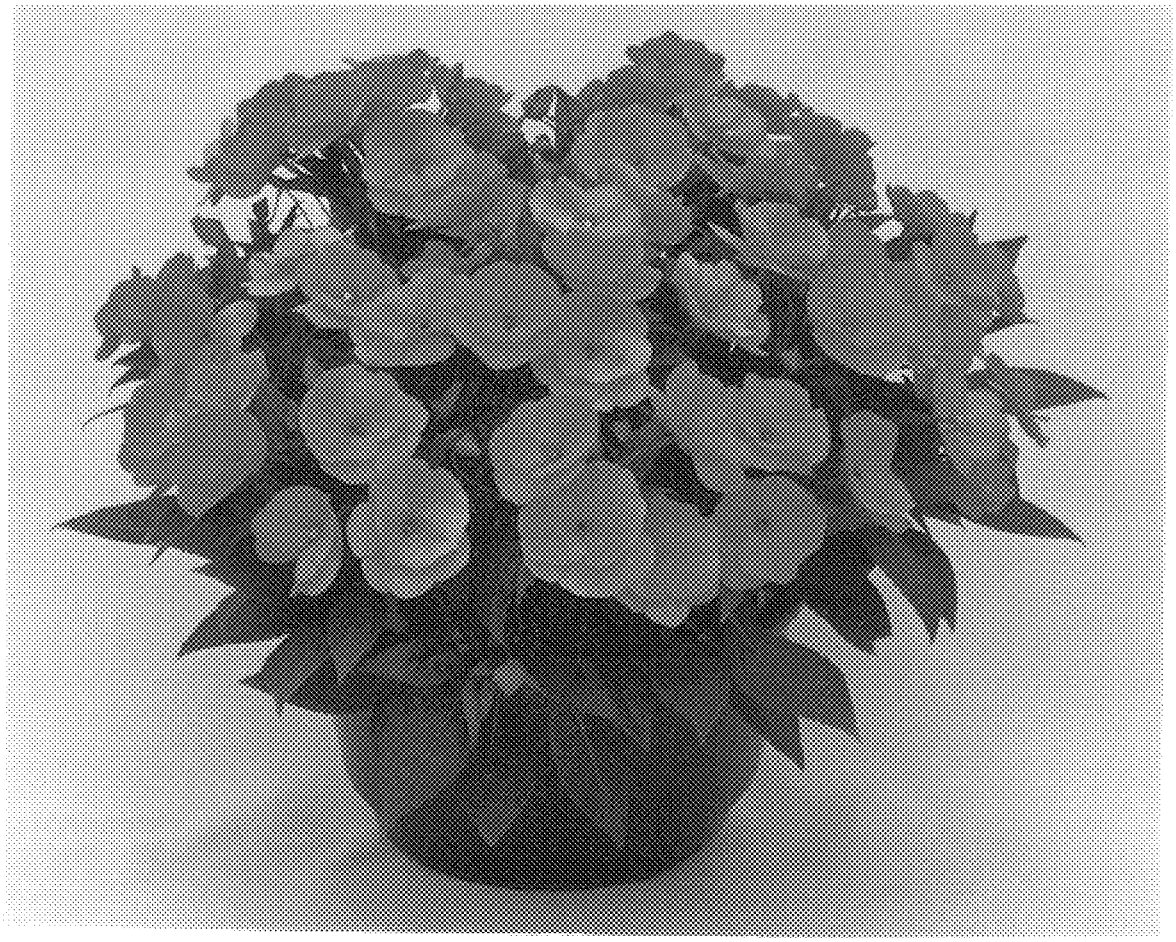
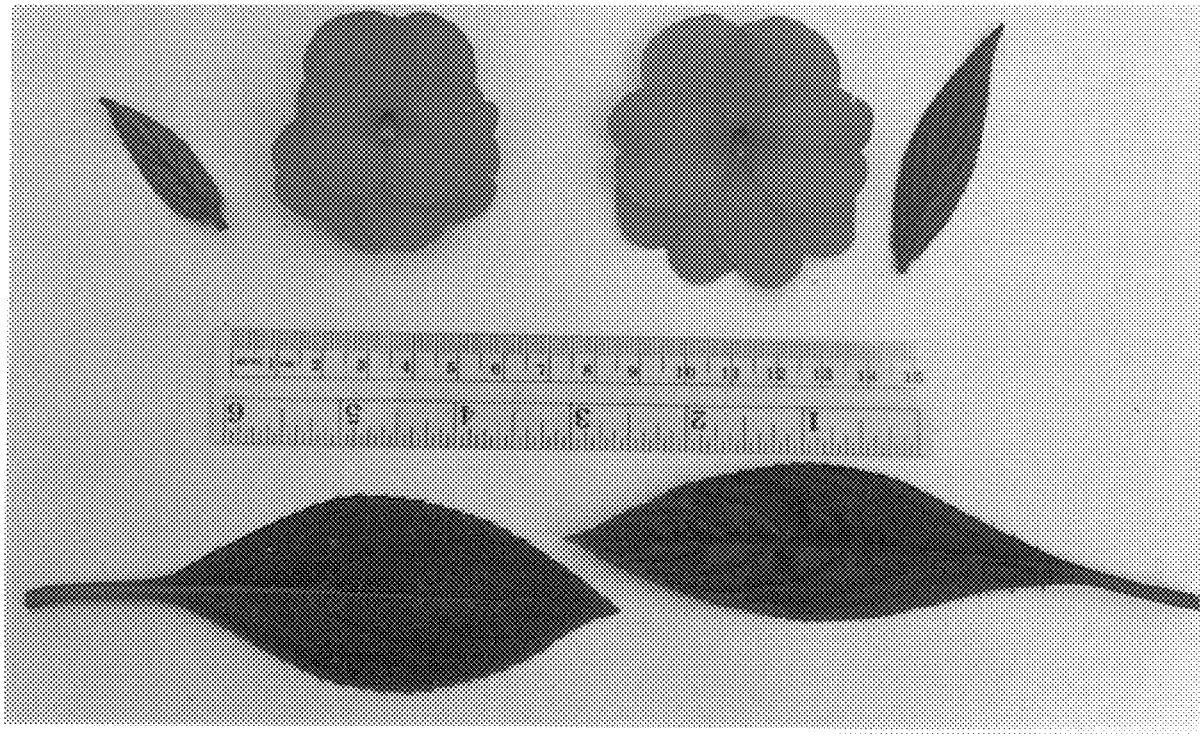

* * * * *